(12) United States Patent
Domb (10) Patent No.: US 7,749,539 B2
(45) Date of Patent: *Jul. 6, 2010

(54) POLYMERIC FORMULATIONS FOR DRUG DELIVERY

(75) Inventor: Abraham J. Domb, Efrat (IL)

(73) Assignee: Efrat Biopolymers Ltd. (IL)

( * ) Notice: Subject to any disclaimer, the term of this patent is extended or adjusted under 35 U.S.C. 154(b) by 1099 days.

This patent is subject to a terminal disclaimer.

(21) Appl. No.: 10/763,876

(22) Filed: Jan. 23, 2004

(65) Prior Publication Data

US 2004/0161464 A1    Aug. 19, 2004

Related U.S. Application Data

(63) Continuation-in-part of application No. 10/433,143, filed as application No. PCT/IL01/01103 on Nov. 27, 2001, now Pat. No. 7,297,347.

(60) Provisional application No. 60/442,799, filed on Jan. 23, 2003.

(30) Foreign Application Priority Data

Nov. 30, 2000    (IL) ..................................... 140017

(51) Int. Cl.
*A61K 9/14* (2006.01)
*C08G 63/06* (2006.01)

(52) U.S. Cl. ...................... 424/486; 424/484; 424/485; 528/205; 528/361

(58) Field of Classification Search ................. 424/486, 424/489, 485, 484; 514/44, 12; 528/205, 528/361

See application file for complete search history.

(56) References Cited

U.S. PATENT DOCUMENTS 4,414,381 A * 11/1983 Griffin et al. ................ 526/190

(Continued)

FOREIGN PATENT DOCUMENTS

EP    0 598 131    5/1994

(Continued)

OTHER PUBLICATIONS

Teomim et al. ("Ricinoleic acid-based biopolymers" in the Journal of Biomedical Materials Research, vol. 45, Issue 3, pp. 258-267, John Wiley & Sons, Inc.).*

(Continued)

*Primary Examiner*—Blessing M Fubara
(74) *Attorney, Agent, or Firm*—Pabst Patent Group LLP (57) ABSTRACT

Poly(ester-anhydrides) or polyesters formed from ricinoleic acid and natural fatty diacids and their method of preparation and its use for delivering bioactive agents including small drug molecules, peptides and proteins, DNA and DNA complexes with cationic lipids or polymers or nano and microparticles loaded with bioactive agents are disclosed herein. The drug delivery compositions are administered to a patient in a liquid form, increase in viscosity in vivo to form a drug depot or implant, and are able to release the incorporated bioactive agent for weeks. In the preferred embodiment, the drug delivery formulations are administered by injection. In one embodiment, the compositions are suitable for local or regional delivery of drugs to diseased sites, such as treating solid tumors and bone infections. In a preferred embodiment, the drug delivery compositions are suitable for site-specific chemotherapy for the treatment of solid tumors including: squamous cell carcinoma (SCC) of the head and neck, prostate cancer, and sarcomas for intratumoral injection or insertion.

21 Claims, 1 Drawing Sheet

U.S. PATENT DOCUMENTS

| | | | | |
|---|---|---|---|---|
| 4,999,417 | A | | 3/1991 | Domb |
| 5,171,812 | A | * | 12/1992 | Domb .................... 526/318.2 |
| 5,179,189 | A | | 1/1993 | Domb et al. |
| 5,473,103 | A | * | 12/1995 | Domb et al. ................ 562/509 |
| 5,480,787 | A | * | 1/1996 | Negishi et al. .............. 435/134 |
| 5,565,188 | A | * | 10/1996 | Wong et al. .............. 424/9.411 |
| 5,626,862 | A | * | 5/1997 | Brem et al. ................ 424/426 |
| 5,648,096 | A | * | 7/1997 | Gander et al. ............... 424/489 |
| 5,756,652 | A | * | 5/1998 | Storey et al. ................ 528/361 |
| 5,846,565 | A | * | 12/1998 | Brem et al. ................. 424/486 |
| 5,859,271 | A | * | 1/1999 | Franson et al. .............. 554/223 |
| 6,303,138 | B1 | * | 10/2001 | Peterson et al. ............ 424/426 |
| 6,306,403 | B1 | * | 10/2001 | Donovan ................ 424/239.1 |

FOREIGN PATENT DOCUMENTS

| | | |
|---|---|---|
| WO | WO 93/05096 | 3/1993 |
| WO | WO 96/22270 | 7/1996 |

OTHER PUBLICATIONS

Domb et al. ("Biopolymers as drug carriers and bioactive macromolecules" in Acta Polymerica, Dec. 14, 1998, vol. 49, Issue 10-11, pp. 526-533).*

Teomim et al. ("Ricinoleic acid-based biopolymers" in the Journal of Biomedical Materials Research, vol. 45, Issue 3, pp. 258-267, John Wiley & Sons, Inc.).*

Domb et al. ("Biopolymers as drug carriers and bioactive macromolecules" in Acta Polymerica, Dec. 14, 1998, vol. 49, Issue 10-11, pp. 526-533).*

O'Hagan, ("Microparticles and polymers for mucosal delivery of vaccines," in Advanced Drug Delivery Reviews, Dec. 1, 1998, pp. 305-320.*

Bremer & Osmundsen, "Fatty acid oxidation and its regulation," in *Fatty Acid Metabolism and Its Regulation* (Numa, ed.) Elsevier: New York, p. 113-154 (1984).

Dang, et al., "Effects of GLIADEL wafer initial molecular weight on the erosion of wafer and release of BCNU," *J. Control. Rel.* 42: 83-92 (1996).

Domb & Langer, "Polyanhydrides. I. Preparation of high molecular weight polyanhydrides," *J. Polym. Chem.* 25: 3373-3386 (1987).

Domb & Maniar, "Absorbable biopolymers derived from dimer fatty acids," *J. Polym. Sci: Polymer Chem.* 31: 1275-1285 (1993).

Domb, et al., "Poly(anhydrides). 3. Poly(enhydrides) based on aliphatic-aromatic diacids," *Macromolecules* 22: 3200 (1989).

Domb, et al., "Polyanhydrides" in *Handbook of Biodegradable Polymers* (Domb, et al., eds.) Hardwood Academic Publishers, p. 135-159 (1997).

Domb, et al., "Polyanhydrides as carriers of drugs" in *Biomedical Polymers: Designed-to-Degrade Systems* (Shalaby, ed.) Hanser Publishers: Munich, p. 69-96 (1994).

Gopferich, in *Handbook of Biodegradable Polymers* (Domb, et al., eds.) Hardwood Academic Publishers, p. 451-471 (1997).

Heller, "Biodegradable polymers in controlled drug delivery," *CRS Crit. Rev. Ther. Drug Carrier Syst.* 1: 39-90 (1984).

Hopfenberg, "Controlled release from erodible slabs, cylinders, and spheres" in *Controlled Release Polymeric Formulations* (Paul, et al., eds.) ACS Symposium Series, Washington DC, 33: 26-32 (1976).

Leong, et al., "Polyanhydrides for controlled release of bioactive agents," *Biomaterials* 7: 364-371 (1986).

Mäder, et al., "In vitro/in vivo comparison of drug release and polymer erosion from biodegradable P(FAD-SA) polyanhydrides—a noninvasive approach by the combined use of electron paramagnetic resonance spectroscopy and nuclear magnetic resonance imaging," *Pharm. Res.* 14(6): 820 (1997).

Park, et al., "Biodegradable polyanhydride devices of cefazolin sodium, bupivacaine, and taxol for local drug delivery: preparation, and kinetics and mechanism of in vitro release," *J. Control. Rel.* 52: 179-189 (1998).

Rosen, et al., "Bioerodible polyanhydrides for controlled drug delivery," *Biomaterials* 4:131-133 (1983).

Teomim, et al., "Perivascular delivery of heparin for the reduction of smooth muscle cell proliferation after endothelial injury," *J. Control Rel.* 60: 129-142 (1999).

Teomim, et al., "Ricinoleic acid-based biopolymers," *J. Blamed. Mater. Res.* 45: 258-287 (1999).

Teomim et al., "Fatty acid terminated polyanhydrides," *J. Polym. Sci.* 37: 3337-3344 (1999).

Tirosh, et al., "Oxidative stress effect on the integrity of lipid bilayers is modulated by cholesterol level of bilayers," *Chemistry and Physics of Lipids* 87:17-22 (1997).

* cited by examiner

FIG. 1

POLYMERIC FORMULATIONS FOR DRUG DELIVERY

CROSS-REFERENCE TO RELATED APPLICATIONS

This application is a continuation-in-part of copending application Ser. No. 10/433,143, entitled "Polyanhydrides", by Abraham J. Domb, filed May 30, 2003, which is a 371 application of WO 02/44232, filed on Nov. 27, 2001, which claims priority to Israeli Application No. 140017, filed on Nov. 30, 2000. This application claims benefit of U.S. Provisional Application No. 60/442,799, filed Jan. 23, 2003.

FIELD OF THE INVENTION

The present invention relates to drug delivery formulations that contain biodegradable polymers and bioactive agents and methods for making these formulations. This application is particularly directed at injectable formulations.

BACKGROUND OF THE INVENTION

There has been extensive research in the area of biodegradable materials for controlled release of drugs. Biodegradable matrices for drug delivery are useful because they obviate the need to remove non-degradable drug depleted devices. The ideal polymeric formulation for delivering drug in a controlled matter would combine the characteristics of a biodegradable polymer carrier that is hydrophobic, be liquid enough to be injected at body temperature but increase its viscosity when injected into tissue to thereby better encapsulate the incorporated drug, be stable under common storage conditions, have a predictable controlled degradation profile, versatile degradation and drug release profiles for both hydrophilic or hydrophobic agents, be safely eliminated from the injection site and the body shortly after the drug has been depleted from the carrier, be made from natural components that degrade and eliminate from the body without causing acute or chronic toxicity, and easy to make at low cost.

A polymer for use in the ideal drug delivery formulation must be hydrophobic so that it retains its integrity and the incorporated drug for a suitable period of time when placed in biological systems, such as the body, and stable at common storage conditions, preferably room temperature for an extended period before use.

The purity of the starting materials used for the preparation of implantable biodegradable polymers is essential because impurities may provoke irritation and local toxicity to the implant site or even systemic toxicity in severe cases. In addition, impurities may affect the structure and physical properties on the polymer such as molecular weight, branching, and formation unwanted chemical bonds.

Many biodegradable polymers have been evaluated for their suitability for use as a matrix for drugs including polyesters, polycarbonates, natural and synthetic polyamides, polyphosphate esters, polyphosphazenes and polyanhydrides. While these polymers were found useful applications as drug carriers, still there is a need for a reliable polymer for short term drug release (i.e. one to twenty weeks) that degrade and eliminated from an implant site within thirty weeks.

Polyanhydrides are useful bioabsorbable materials for controlled drug delivery. They hydrolyze to dicarboxylic acid monomers when placed in aqueous medium. Since their introduction to the field of controlled drug delivery, about 15 years ago, extensive research has been conducted to study their chemistry as well as their toxicity and medical applications. Several review articles have been published on polyanhydrides for controlled drug delivery applications (see Domb, et al., "Polyanhydrides" in *Handbook of Biodegradable Polymers* (Domb, et al., eds.) Hardwood Academic Publishers, p. 135-159 (1997)).

The stability of polyanhydrides in solid state and dry chloroform solution has been studied. Polyanhydrides, such as PSA, decreased in molecular weight over time. The decrease in molecular weight shows first-order kinetics, with activation energies of 7.5 Kcal/mole-° K. The decrease in molecular weight was explained by an internal anhydride interchange mechanism, as revealed from elemental and spectral analysis. A similar decrease in molecular weight as function of time was also observed among the aliphatic-aromatic co-polyanhydrides and imide containing co-polyanhydrides. (Domb, et al., *Macromolecules* 22: 3200 (1989)).

The low melting point and the solubility of aliphatic polyanhydrides in common organic solvents such as methylene chloride, allows for the easy dispersion of drug into the polymer matrix. Drugs can also be incorporated via compression or melt molding processes. For example, drugs can be incorporated into a slab either by melt mixing the drug into the melted polymer or by solvent casting. Polymer slabs loaded with a drug can also be prepared by compression molding a powder containing the drug. Similarly, one can injection mold the drug-polymer formulation into beads or rods. Polymer films can be prepared by solvent evaporation by casting the polymer solution containing the drug onto a Teflon coated dish. Microsphere-based delivery systems can be formulated by common techniques, including solvent removal, hot-melt encapsulation and spray drying. However, it is essential that all processes be performed under anhydrous conditions to avoid hydrolysis of the polymer or absorption of water in the polymer mass which degrade the polymer with time during storage.

The degradation of polyanhydrides, in general, varies with a number of factors. These factors include the chemical nature and the hydrophobicity of the monomers used to produce the polymer, the level of drug loading in the polymeric matrix, the pH of the surrounding medium (the higher the pH, the more rapidly the polymers degrade), the shape and geometry of the implant (the degradation is a function of the surface area) and the accessibility of the implant to water (porous materials will degrade more rapidly than non-porous). The porosity in an implant is dependent on the method of fabrication. For example, a compression-molded device will degrade at a much more rapid rate than an injection molded device due to the presence of a higher porosity in the polymer as compared to the latter.

The degradation rates for a number of polyanhydrides are available in the literature. Most studies focused on the degradation of the clinically tested polyanhydrides, poly(CPP-SA) and poly(FAD-SA). In general, during the initial 10 to 24 hours of water incubation in aqueous medium, the molecular weight dropped rapidly with no loss in wafer mass loss. This period was followed by a fast decrease in wafer mass accompanied by a very small change in polymer molecular weight. The period of extensive mass loss starts when the polymer molecular weight reaches a number average molecular weight (Mn) of about 2,000 regardless of the initial molecular weight of the polymer. During this period which lasts for about one week, sebacic acid, the relatively water soluble comonomer, is released from the wafer leaving the less soluble comonomer, CPP or FAD, which is slow to solubilize (DANG, et al., *J. Control. Rel.* 42: 83-92 (1996)). Increasing the content of sebacic acid in the copolymer increases the hydrophilicity of the copolymer, which results in a higher erosion rate and hence higher drug release rates. This could be explained by the fact that the anhydride linkages in the polymer are hydrolyzed subsequent to penetration of water into the polymer. The penetration of water or water uptake depends on the hydrophobicity of the polymer and therefore, the hydrophobic polymers which prevent water uptake, have slower erosion rates and lower drug release rates. One can alter the hydrophobicity of the polymer by altering the structure and/or the content of the copolymer, thereby being able to alter the drug release rate. Since in the P(CPP-SA) and P(FAD-SA) series of copolymers, a ten-fold increase in drug release rate was achieved by alteration of the ratio of the monomers, both polymers can be used to deliver drugs over a wide range of release rates.

Several attempts were made to improve the physical properties, drug release and storage stability of polyanhydrides by using fatty acid based comonomers, using linear fatty acid chain terminals or by blending the polymers with fats and other biodegradable polymers. U.S. Pat. No. 5,171,812 to Domb et al. describes the synthesis of polyanhydrides from dimer and trimer erucic acid. These polymers were amorphous with a crystallinity in the range of 20%, hydrophobic and pliable and released the incorporated drugs for a few weeks in buffer solutions. However, these dimer fatty acid based polymers were not stable on storage at room temperature or refrigeration and rapidly decreased in molecular weight which requires storage under freezing conditions (−20° C.). Another major problem occurring with this class of polymers is their incomplete degradation and elimination from dogs after subcutaneous or intramuscular implantation probably due to the C—C bond between the two connected fatty acids.

To solve the problem of the FAD polymer elimination in vivo, diacid fat with hydrolyzable ester bond has been synthesized and evaluated as carrier for drugs. Polyanhydrides synthesized from nonlinear hydrophobic fatty acid esters based on ricinoleic, maleic acid and sebacic acid, possessed desired physico-chemical properties such as low melting point, hydrophobicity and flexibility to the polymer formed in addition to biocompatibility and biodegradability. Although these polymers were fully degradable in vivo with suitable properties as drug carriers, the major problem of storage stability and the high polydispersity remain. These polymers' molecular weight was drastically decreased within 2-3 days when stored at room temperature and the polydispersity was over 10. It was thought that a liquid polymer may release the incorporated drug too rapidity as is the case when using fatty oils.

Another attempt to obtain stable polyanhydrides that are useful for controlled drug delivery was the formation of polyanhydrides with linear fatty acid terminals (U.S. Pat. No. 5,179,189 to Domb et al.). This patent describes linear polyanhydrides made of aliphatic or aromatic diacids terminated with linear fatty acids such as stearic acid. Although these polymers possess longer drug release period and degradation time, they remain crystalline (>50%) and not pliable similar to the corresponding polymers with acid or acetyl terminals. More important, the polymers are not stable at room temperature or at refrigeration and depolymerize and hydrolyze to a low molecular weight polymer a few days of storage and form a fragile and easy to crumble polymer mass. Another attempt was the blending of polyanhydrides with biodegradable polyesters or fatty acids and triglycerides. The resulting polymeric mixtures did not form uniform blends, the polyanhydride component in the mixture degraded at a similar rate as the pure polymer leaving the hydrophobic component intact, and the storage stability did not improve.

While hundreds of polyanhydride structures are available for use as drug carriers, they suffer from a few major limitations as practical carriers for drugs. First, many of them are made of synthetic monomers, such as aromatic and heterocyclic diacid monomers, which present a risk of toxicity and slow elimination rate from an implanted animal or human (these hydrophobic co-monomers are used to control the drug release and polymer degradation). Second, these polymers are highly sensitive to heat and moisture, which makes them unstable at room temperature or even at refrigeration storage conditions which require storage at −20° C. or below. This storage stability problem is essential for a medical product to be distributed to hospitals, distribution and storage at −20° C. is very difficult logistically, expensive and impractical. The only polyanhydride device in clinical use is the GLIADEL® brain implant, which is manufactured by GUILFORD PHARMACEUTICALS®. This product requires an all time storage at −20° C. because at higher temperatures, the molecular weight of the polymer carrier drops to below 20,000 which affects the drug release rate and rejection of the device. A third problem with polyanhydrides is that polymers made of linear aliphatic acids are crystalline and fragile, which makes them impractical for use as drug carriers as they may fragment during shipment or use. The polymers used for controlled drug delivery have been solids that have to be inserted in the body during or by surgical intervention.

The presently available injectable formulations for controlled drug delivery have significant limitations. For example, ATRIGEL® (ATRIX LABORATORIES, INC.) is an injectable formulation based on a solution of poly(lactic acid) in the organic solvent, N-methylpyrrolidone (NMP). This formulation has been used for the delivery of cisplatin aminocycline, LHRH peptide and other drugs. The main limitation of this formulation is the use of NMP, an organic solvent, which must be diffused in tissue in order for the polymer to solidify into a solid delivery system. During the diffusion of the solvent out of the formulation, the drug is also washed out from the formulation which may cause a high drug release immediately after injection. REGEL® (MACROMED, Inc.) is a formulation for paclitaxel based on micellar poly(ethylene glycol) and poly(lactic acid) block copolymers (PEG-PLA) solution in water that gel in the body is now under development for treating solid tumors. This formulation is a dispersion of a polymer is water medium. Like formulation uses solvents in order to obtain a liquid formulation that can be injected and solidify into a gel in the body due to solvent extraction or temperature phase change.

There remains a strong need for an injectable liquid polymeric formulation that can be injected into solid tumors or tissue with versatility in polymer degradation and drug release profile which is stable at non freezing conditions.

It is therefore on object of the invention to provide improved injectable polymeric drug delivery formulations that are stable at non-freezing temperatures and deliver drug without causing toxicity to the patient.

It is a further object of the invention to provide improved methods for drug delivery.

BRIEF SUMMARY OF THE INVENTION

Poly(ester-anhydrides) or polyesters formed from ricinoleic acid and natural fatty diacids and their method of preparation and its use for delivering bioactive agents including small drug molecules, peptides and proteins, DNA and DNA complexes with cationic lipids or polymers or nano and microparticles loaded with bioactive agents are disclosed herein. The drug delivery compositions are administered to a patient in a liquid form and are able to release the incorporated bioactive agent for weeks, which is even longer than solid polymers prepared from the same monomers. The reason for the slow release is an unexpected phenomenon of increasing the viscosity of the polymer formulation when placed in aqueous medium such as buffer solution, tissue or biological mediums. This increase in viscosity results in a semisolid compact implant that keeps its integrity while slowly degrading and releasing the incorporated drug and eliminating from the body. In the preferred embodiment, the drug delivery formulations are administered to a patient by injection. In one embodiment, the compositions are suitable for local or regional delivery of drugs to diseased sites, such as treating solid tumors and bone infections. In a preferred embodiment, the drug delivery compositions are suitable for site-specific chemotherapy for the treatment of solid tumors including: squamous cell carcinoma (SCC) of the head and neck, prostate cancer, and sarcomas for intratumoral injection or insertion.

DETAILED DESCRIPTION OF THE INVENTION

I. Drug Delivery Compositions

The drug delivery composition contains a biodegradable polymer matrix loaded with an active agent, such as anticancer agent. The compositions is administered in a liquid or pasty form and increases its viscosity administration to form a semisolid depot or implant. The active agent is homogeneously dispersed into the polymer matrix at room temperature. The active agent is released in a controlled manner to the surrounding tissue, when placed in contact with body fluids, while the polymer carrier eliminates itself by slow degradation.

1. Polymers

The polymers used in the drug delivery compositions are poly(ester-anhydrides) or polyesters formed from ricinoleic acid and natural fatty diacids. In a preferred embodiment, the poly(ester-anhydrides) have the following general structure:

where R is a linear or branched aliphatic or aromatic moiety when x+y=1 and x is not 0, or R is an unsaturated fatty acid with at least one cis-double bond, or an ester of ricinoleic acid when x+y=1. R' is a ricinoleic acid residue, and R" is an aliphatic or aromatic moiety. n is an integer from 1 to 200. x and y are in a ratio suitable for providing an injectable pasty polymer.

The polymers are of controlled hydrophobicity which is affected by the ratio of the ricinoleic acid to the fatty acid acid in the polymer when ricinoleic acid is part of the polymer backbone or the terminal groups to the polymer chain and the hydrophobicity of the terminal group (length and structure of the hydrocarbon) for terminated polymers.

As used herein, the term "aliphatic" refers to a linear branched of cyclic alkane, alkene or alkyne. Preferred aliphatic groups in the disclosed polyanhydrides are $C_4$ to $C_{22}$ alkyls moieties. The terms "liquid polymer", "pasty polymer" or "injectable polymer formulations" refers to compositions that are liquid enough to be injected using a syringe at a temperature of 37° C. or below.

As used herein the term "non-linear hydrocarbon" refers to an alkyl chain with at least one cis-double bond or at least one more branching chain which together hydrolyze into safely eliminated molecules when implanted in a body of an animal or human.

The biodegradable compositions disclosed here are poly (ester-anhydrides) which are formed by melt or solvent polycondensation of aliphatic or aromatic diacids or hydroxy acids and ricinoleic acid to form a liquid polymer. In one embodiment the poly(ester-anhydride) is prepared from a polyanhydride and ricinoleic acid, wherein the concentration of ricinoleic acid is at least 90% by weight of the polymer. The mono acid non-linear hydrocarbons act as molecular weight controllers which limit the molecular weight to about 10,000. This relatively low but controlled molecular weight and low polydispersity, are less sensitive to depolymerization and are more stable to hydrolysis due to their hydrophobic terminals. The non-linear structure provides a range of new properties including: various degradation times and drug release profiles, and reduced melting temperature and crystallinity due to irregularity induced by the bend terminals or side chains.

2. Active Agents

The polymeric drug formulations may contain one or more active agents, such as small drug molecules, peptides and proteins, DNA and DNA complexes with cationic lipids or polymers. Anticancer agents include of taxans and taxan derivatives, platin derivatives, vinca alkaloids, antimetabolites, anticancer peptides and proteins, and DNA and antisense active in treating solid tumors; paclitaxel, cisplatin, carboplatin, 5-fluorouracil, methotrexate, doxorubicine, vincrystine, etoposide, and other anticancer agents and combinations thereof. The drug can also be an anti multi-drug-resistance (MDR) agent, or an agent that improves the effectiveness of the anticancer agent.

Other therapeutic agents active, including peptides, proteins, oligonucleotides, polynucleotides, and plasmids, may be incorporated in the polymer to form the drug delivery compositions. Peptides may have a wide range of sizes, such as from a dipeptide to a peptide containing 1,000 amino acids. Examples of suitable peptides include insulin, leutenizing hormone releasing hormone (LHRH), somatostatin, thyroid releasing hormone (TRH), and growth hormone, may be included in the formulation. The active agents may be antibacterial agents, anti-inflammatory and anticancer agents, antidepressants, analgesics, or local anesthetics. Examples of such active agents, include aminoglycoside antibiotics, quinoline antibiotics, antimicrobial agents, antifungal agents and antiviral agents, lidocaine, bupivacaine, non-steroidal anti-inflammatory drugs, steroids, morphine and narcotic agents, antidepressants, risperidol and other drugs intend to improve mental behavior, risporidol, tetracycline, chlorhexidin, and aminocycline. In the preferred embodiment the active agent is a drug from the family of taxans, platin derivatives or antimetabolites. A list of active agents for treating various diseases, including solid tumors can be found in updated textbooks and medical codex, for example: Martindale—The Extra Pharmacopoeia, and the National formulary (NF).

The active agents may be incorporated in the polymer by direct mixing or by first interacting these active agents with polycations and stabilizing agents prior to incorporation in the polymer. In one embodiment, the active agent is added as a powder to the polymer and mixed until an homogeneous uniform injectable paste is obtained.

Optionally, the drug is encapsulated, such as in polymeric microparticles or nanoparticles (e.g. nanospheres and microspheres) or in a complex form, prior to being incorporated in the polymeric drug delivery formulation.

3. Additives, Excipients and Carriers

The drug delivery formulation may contain excipients, such as stabilizers for the active agent, and/or carriers. Pharmaceutically acceptable additives that improve uniformity and physical and chemical stability at storage may be included in the formulation. Hydrophilic additives, including short chain polyethylene glycol, poloxamer, and thin powder of sugars or salts, may be added to the formulations to modify the rate of drug release. Additives include surfactants, inert hydrophilic substances, inert hydrophobic substances, and stabilizers. Suitable surfactants include Tween, Span, poly (ethylene glycol), poly(ethylene glycol)-fatty chain, copolymers of ethylene glycol and propylene glycol, phospholipids, and pharmaceutically acceptable surfactants. Hydrophilic substances include poly(ethylene glycol), copolymers of ethylene glycol and propylene glycol, mono-, oligo- and polysaccharides, inorganic salts, and polyols.

II. Methods of Making the Polymers

1. Purification

Methods for economically purifying ricinoleic acid have been developed. The purified ricinoleic acid is useful for the formation of poly(ester-anhydrides) based on ricinoleic acid for use in drug delivery. Ricinoleic acid is produced from the hydrolysis of castor oil which may contain protein contaminants, as well as fatty acids that are not ricinoleic acid, more than 15% w/w of the oil. Pure ricinoleic acid at a 98% pure is available at a cost of $60,000 per Kg, while the technical grade cost about $90 per Kg. A simple and reliable purification method for ricinoleic acid from the technical grade acid was therefore developed. Various methods were used, including chromatography, extractions, precipitation, distillation and other chemical methods including bringing the hydroxyl of ricinoleic acid to a solid support such as poly(maleic anhydire-methyl vinyl ether), via the hydroxyl group of ricinoleic acid, the unbound acids filtered out, and the support washed with a solvent. In a similar manner, ricinoleic acid is esterified by a hydrophilic acid such as carboxylic acid terminated polyethylene glycol or muconic acid. The hydrophilic derivative is then extracted with water where the fatty acids that do not have an hydroxyl group will remain water insoluble. In the next step, the hydrophilic ester is hydrolyzed to produce pure ricinoleic acid. The preferred methods for ricinoleic acid purification from an economic viewpoint and ease of workup are chromatography of ricinoleic acid or its ester, or precipitation-extraction of the metal salt of ricinoleic acid. Salts of ricinoleic acid can be prepared from the reaction of ricinoleic acid with sodium, calcium or potassium hydroxide in lower alcohol, ethanol, methanol, propanol, and butanol, or in an aqueous solution. The salt that precipitates from the solution is then extracted with petroleum ether or with isopropyl or ethyl ether. The pure ricinoleic acid salt is than acidified to form the free ricinoleic acid.

2. Synthesis of Polymers

The polymers can be prepared by several methods. The diacid and monoacid molecules are refluxed together in acetic anhydride for 20 min. and the solvent is evaporated and vacuum is applied to yield the molten polymer. Alternatively, the diacid monomer and the mono acid terminal are activated by acetic anhydride to form the diacid prepolymer and the acetate anhydride derivative of the nonlinear hydrocarbon which is then mixed at a desired ratio and polymerized at 150° C. under a vacuum of about 0.5 mm Hg. Another way of effecting polymerization is the use of a dehydrating agent that removes a water molecule from two acids to form the anhydride bond.

Figure 1:
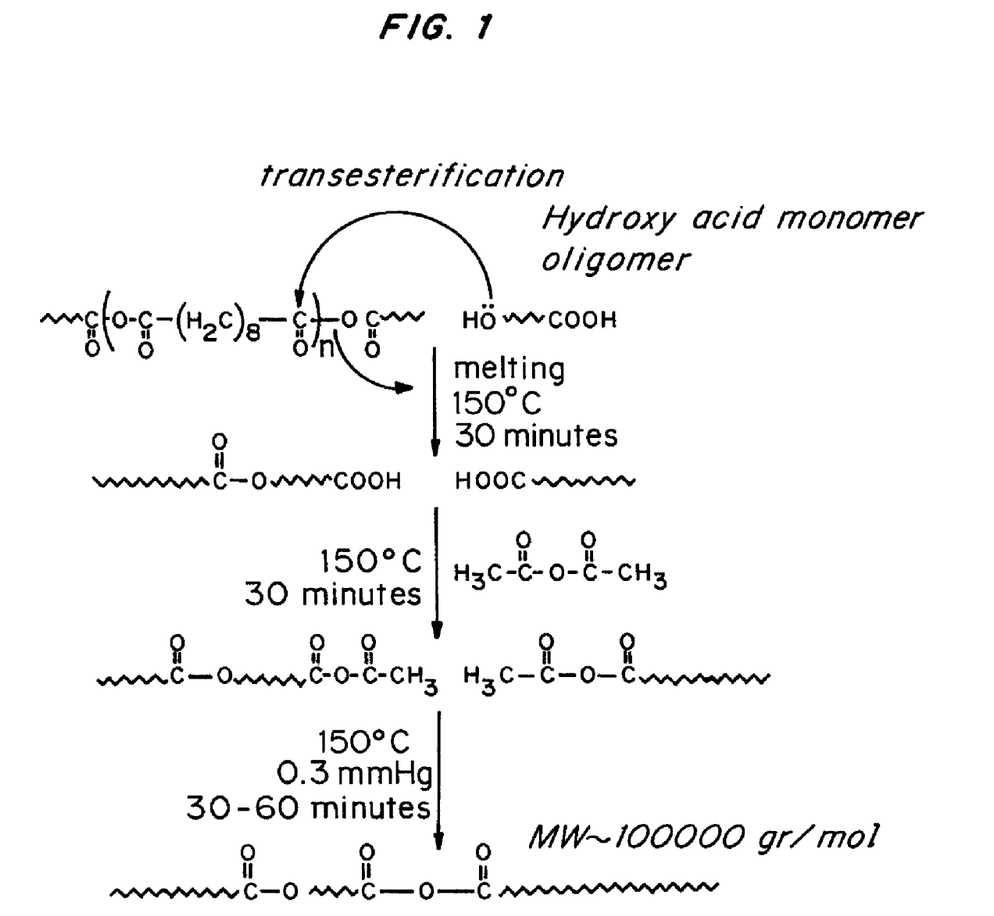
FIG. 1 is a chemical synthesis for producing poly(ester anhydrides).

A standard chemical synthesis for poly(ester-anhydrides) is described in FIG. 1. Biodegradable poly(ester-anhydride) with ester bonds along the polymer chain are preferably prepared by:

a. synthesizing a polyanhydride at a degree of polymerization (n) of 20 to 10,000;

b. reacting the polyanhydride of Step a with ricinoleic acid to form polyanhydride ester bonds with carboxylic acid terminals; and c. polymerizing the carboxylic acid terminated polymer of Step b to form a higher molecular weight polyanhydride.

In addition to the ricinoleic acid added in step b, other hydroxy acid or amino acid molecules can be add to the reaction mixture. Examples include lactic acid, glycolic acid, hydroxybutyric acid, hydroxycaproic acid, hydroxybenzoic acid, and their oligomers, mucic acid, tartaric acid, and pentahydroxycyclohexane carboxylic acid, γ-amino butyric acid, β-alanine and natural α-amono acids.

Biodegradable poly(ester-anhydrides) with unsaturated fatty acid terminals are prepared from the polycondensation reaction between the acetate anhydride activated diacid prepolymers, and unsaturated fatty acids such as oleic acid, ricinoleic acid or O— esters of ricinoleic acid that act as chain terminators.

Dicarboxylic acid monomers: monomers useful for the synthesis of this polymer are aliphatic diacids of the structure: HOOC—R—COOH where R is a linear or branched chain such as: linear alkane dicarboxylic acids of $C_4$ to $C_{22}$; dimer fatty acids such as dimer erucic acid or oleic acid; non-linear fatty acid-ester derivatives such as ricinoleic acid, fumarate or succinate; and cyclohexane or cyclopentane derivatives. R can be a polymeric chain with carboxylic acid terminals such as oligomers and polymers made of lactic acid, glycolic acid, hydroxy-butiric acid, caprolactone, and trimethylene carbonate having two carboxylic acid terminals.

Unsaturated fatty acids may include: ricinoleic acid, oleic acid, arachidonic acid, linoleic acid, linolenic acid, and other fatty acids with at least one cis-double bond; alkyl O-esters and carbonates of ricinoleic acid, oligo(hydroxy alkanoic acid)—O-esters and carbonates of ricinoleic acid. The physical properties of the polymers can be manipulated by careful selection of the degree of branching (2-4 arms), the chain length and the nature of the hydrocarbons of each arm and the content of the terminals in the polymer.

Polyesters pastes based on ricinoleic acid and alkyl hydroxyl acids may be prepared by direct polycondensation of ricinoleic acid and alkyl hydroxyl acid such as lactic acid, hydroxyl butyric acid and glycolic acid at a ratio that forms a paste, usually at an amount of at least 10% w/w of ricinoleic acid is needed. In an another method, ricinoleic acid lactone is prepared and ring opening copolymerized with cyclic alkyl hydroxyl acids or carbonates such as lactide glycolide, trimethylene carbonate and caprolactone using common catalysts such as stannous octoate. The third method is trans-esterification and re-polyesterification similar to the method described above for the insersion of ricinoleic acid in a polyanhydride. In this method, a polyester such as poly(lactide) is reacted with ricinoleic acid in bulk or in solution to form shorter chains by trans esterification. The hydroxyl-acid terminated oligomers containing a ricinoleic acid terminal is now repolymerized into a polyester by direct condensation or after activation of the carboxylic acid end groups. The resulted product is a polyester with ricinoleic acid groups along the polymer chain. The amount of ricinoleic acid along the chain as well as the polymer molecular weight determines the melting point and consistency of the resulted polymer. In general, the inclusion of 10% w/w ricinoleic acid reduces significantly the melting point of the polymer.

Transesterification of poly(sebacic acid) (PSA) is a one-pot reaction that starts with a high molecular weight polymer based on anhydride bonds and yields polymer based on random anhydride ester bonds. In order to convert poly(anhydride) to poly(ester-anhydride), the polymer is reacted with ricinoleic acid (RA). The hydroxyl group of RA attacks the anhydride bond in a transesterification reaction. The products of the reaction are carboxyl group ended oligomers based one pure anhydride bonds or random mixed ester anhydride bonds.

In principal, any hydroxy alkyl acid is suitable for that type of reaction. The purpose of the final product (biodegradable polymer for drug delivery) limits one to non-irritant and pure hydroxy acids.

Fast eroding polymers are suitable candidates to control drug release through erosion mechanism. Those are polymers that have a fast hydrolyzing bond, such as polyanhydrides. Incorporation of ester bonds into anhydride framework reduces the rate of hydrolysis because ester bonds hydrolyze slower then anhydride bonds. However, the polymers still have all of the properties of a biodegradable polymer that anhydride bonds provide.

III. Methods of Using the Drug Delivery Compositions

The drug delivery composition is administered in a liquid or pasty form to a patient by injection, such as by using a syringe. For example, the formulation may be prefilled in a syringe with a needle that allows administration to solid tumors by injection. The formulation may be injected intraperitoneally, intradermally, intramuscularly, intratumorally, into body cavities, into bone, or into internal organs.

After administration, the viscosity of the composition increases, and the composition forms a semisolid drug depot or implant. The depot or implant slowly degrades and is completely eliminated from the body. As the depot or implant degrades, the drug is released. The degradation and release of drug occurs over a period of time ranging from days to weeks. Typically the drug will be released over a time period ranging from one to thirty weeks, preferably from one to twenty weeks. For regional drug delivery regimes, the drug is preferably released for periods ranging from one week to about eight weeks.

1. Treatment of Cancer

Cancer of the head and neck accounts for about 40,000 new cases every year in the US, which is about 5% of all new cancer cases in the US. Unlike other solid tumors, the most common manifestation of recurrence of head and neck cancer is regional, that is, recurrence in the neck. The current treatments, which includes surgical removal of the tumor, systemic chemotherapy, and radiotherapy, has demonstrated some effectiveness in inducing tumor regression, especially in the early stage of the disease but has a high rate of recurrence in the late stages. An attractive alternative is the local administration of the agent from a polymeric delivery system implanted at the site of the tumor during resection surgery. In this fashion, the drug depot can maintain a high local concentration to prevent local tumor recurrence. This also allows the use of a variety of agents whose diffusion is not restricted by a poor blood supply secondary to a prior radiation therapy or scarring from prior surgery.

The same formulation can also be applied for treating other solid tumors including: pancreas, prostate, breast, bone, brain, colon cancers and sarcomas. Cancer of the pancreas accounts for approximately 70,000 new cases every year in the US, Europe and Japan. The other cancers account for about 400,000 new cases each year in the US. Prostate cancer is the second highest type of cancer in men. The incidence of prostate cancer continues to rise each year due to an increased awareness of the disease and an aging population. Over the past decade, substantial improvements in diagnosis and staging of the disease have been made with the combined use of digital rectal examination, measurement of serum PSA levels, and transrectal ultrasound. Earlier diagnosis of prostate cancer has resulted in a state migration, with an increased proportion of men diagnosed with clinically localized disease and a 50% decrease in the incidence of stage D2 disease over the last two years. Hence, most men diagnosed with prostate cancer during the 1990's were found to have localized disease. The natural history of localized prostate cancer is variable but is generally one of slow local progression with later development of regional metastasis. More then two-thirds of patients will suffer local or systemic progression, and more than half of with prostate cancer will die from their disease within ten years. Significant morbidity can result from local tumor progression, including bladder outlet and urethral obstruction, pain and bleeding. Although radical prostetectomy and radiation therapy are both effective forms of treatment, both have low but significant morbidity and not all patients are suitable candidates. In addition, serum PSA measurement allow for the detection of biochemical and local recurrences after radiotherapy and identify men destined to experience disease recurrence, who may benefit from early and additional adjuvant therapy. Androgen withdrawal therapy remains the only efficacious treatment for advanced or recurrence prostate cancer. However, both surgical castration and LHRH agonist treatment are associated with significant long term side effects. Moreover, about 15% of the new cases do not respond to hormone and for the treated patients, over time the tumor becomes hormone resistant. Therefore, development and utilization of therapeutic strategies are essential for the treatment of this pathology.

Recently, several monoclonal antibodies have been shown successful for the treatment of breast cancer. Specifically one monoclonal raised against the extracellular domain of the growth factor ErbB2 has been shown to stimulate down regulation of receptor and reduction in tumor development. This protein-based therapeutic strategy specifically fits patients with recurrent localized tumors after radiotherapy. Some patients with localized tumors who are not candidates for aggressive therapy would benefit from additional well-tolerated, minimally invasive, local treatment modalities. Also, the local combination of chemotherapy with protein therapy may be offered as a first treatment to delay the use of hormones, particularly for the young patients.

The anatomical location of the prostate gland is amenable to direct local injection with agents capable of inducing apoptosis. Brachytherapy for localized prostate cancer is now performed by transperineal placement of radioactive seed implants under transrectal ultrasound guidance. The prostate gland could also be infiltrated with chemotherapeutic agents using similar techniques. Paclitaxel has been described previously to have cytotoxic activity against a number of prostate cancer cell line in vitro and in vivo. Cisplatin, 5-FU, and MTX have also been used for treating solid tumors and prostate cancer.

The narrow therapeutic index of anticancer drugs delivered systemically is associated with significant side effects. These may occur even at therapeutic concentration in the systemic blood and are extremely exaggerated at elevated concentration. Another complexity of chemotherapy is the high extent of intra- and inter-patient variability in pharmacokinetics of anticancer drugs. Pharmacokinetic studies indicate highly variable absorption, tissue distribution and elimination for most anticancer drugs. Several-fold differences in the drug clearances within a homogeneous patient population have been observed for major anticancer drugs.

Cisplatin and carboplatin are cell cycle-non-specific agents, and the total cytotoxic effect of a given dose is independent of the schedule of administration. The major adverse effects of cisplatin are renal, neurologic and ototoxicity, and are correlated to both Cmax and total exposure to the drug indicated by the area under the concentration-time curve (AUC). The toxicological properties of carboplatin differ from that of cisplatin, and its primary dose-limiting toxicity is thrombocytopenia. Paclitaxel is an antimicrotubule antineoplastic agent is a cell cycle-specific, as it blocks cell replication in the late G2 phase and M phase of the cell cycle. It has also antiproliferative, antiangiogenic and antimetastatic properties which significantly improve its efficacy in anticancer therapy. The major dose-limiting adverse effect of paclitaxel is bone marrow suppression, manifested by neutropenia, leukopenia thrombocytopenia, and anemia. Other adverse reactions are: hypersensitivity, most likely due to Chremophor EL (a component in the current pharmaceutical formulation) of paclitaxel; dose-dependent nervous system effects; cardiotoxicity, mostly nonspecific repolarization, sinus bradycardia, sinus tachcardia and premature beats; hepatotoxicity and alopecia.

Chemotherapy is based, in general, on combinations of anticancer agents. This is mainly done to minimize the dose of each agent, reduce toxicity and produce a synergetic cytotoxic effect. The combination of platinum compounds and paclitaxel is common, and shown to be very effective. Additional adjuvant drugs including vasoconstrictor agents and MDR inhibitors can be included in the polymer formulation. In certain cases, prolonged exposure of tumor cells to chemotherapy, with certain anticancer agents (e.g. paclitaxel), induces a multi-drug resistance (MDR) which is exhibited by a declined response of the tumor to the anticancer drug. In these cases most of the anticancer agents associated with development of MDR tend to be substrates of the P-glycoprotein (Pgp) efflux system. If any MDR type resistance emerges in response to the treatment, this can be minimized by concurrent administration of Pgp inhibitor agents (e.g., cyclosporin or verapamil). This approach takes advantage by this local mode of administration of the high local concentration of the Pgp inhibitor that can be produced with minimal systemic concentrations.

The drug delivery formulation is administered to a patient in the form of a liquid or pasty polymer. Preferably, the formulation is injected into the tissue site. The drug may be administered to or adjacent to the cancer or region where the cancer has been resected. After administration, the formulation's viscosity increases and it forms a semisolid implant. In the case of treating solid tumors, the implant provides a high dose of anti-cancer drug for an extended period of time, in the tumor site, with minimal systemic drug distribution, thus, providing a localized treatment of the residual tumor cells as a complementary drug therapy to the surgical procedure of tumor removal or intratumoral injection for non-operable tumors. The same concept of long term drug delivery to specific diseased body sites applies also to any solid tumors or other localized diseases. In the preferred embodiment, the drug is administered to treat solid tumors including: squamous cell carcinoma (SCC) of the head and neck, prostate cancer, and sarcomas for intratumoral injection or insertion. The formulation may be administered to treat cancer of the gastrointestinal tract.

2. Treatment of Other Diseases and Disorders

Other drugs may be included in the injectable drug delivery formulations and these formulations may be used to treat a wide variety of diseases and disorders. For example, the drugs may be an antibiotics for treating osteomyelitis, soft tissue infections, gingivitis, and other local bacterial infections. The drugs that may be used are from the family of aminoglycosides, quinolines and other antibiotics. The injectable formulation can be used for the local delivery of local anesthetic and analgesics such as bupivacaine, lidocaine and ibuprofen. Antidepressants, antiepileptic agents and other drugs that are used to treat brain disorders. Risperidol is an example of a drug that requires an extended release formulation. The drug delivery system can be used for the delivery of peptides and proteins by simple mixing the protein in the liquid polymer without any heat of organic solvents, and thus the protein is stable during the process of incorporation in the polymer.

EXAMPLES

Example 1

Purification of Ricinoleic Acid

Two methods were used to purify ricinoleic acid that is used for polymer synthesis. In the first method, separation by chromatography of the ester derivative of ricinoleic acid and hydrolysis is performed.

Method I: Purification by Chromatography:

a. Preparation of ricinoleic acid ester: 100 grams of ricinoleic acid (Acros, or Fluka, 0.335 mole) was dissolved in 300 ml of absolute methanol. The mixture was cooled to 0° C. (ice bath) and gaseous HCl was allowed to pass through the mixture during 20-30 minutes. After, the mixture was allowed to stir at room temperature for 2 h and diluted with DDW (500 ml). The combined water-methanol mixture was transferred to 1 L separation funnel and the obtained ricinoleic acid methyl ester was extracted from the mixture with hexanes (200 ml). The hexanes extracts were washed with deionized water (2×100 ml) and with 10% (w/v) $NaHCO_3$ and treated with anhydrous $MgSO_4$, filtered and evaporated to dryness.

Yield=102 grams of ricinoleic acid methyl ester (~97%).

TLC (10% acetone in hexanes) showed two major spots:

(1) Rf=0.75; methyl esters of non-hydroxy fatty acids (i.e. oleic, linoleic, stearic, etc.).

(2) Rf=0.375; methyl ester of ricinoleic acid b. Purification of ricinoleic acid methyl ester:

The crude ricinoleic acid methyl ester was separated by silica-gel column chromatography (400 grams of silica-gel dissolved in hexanes, column dimensions=70×550 mm). The crude product was diluted with hexanes (50 ml) and introduced to the column. The column was eluted as follows:

(1) Hexane (2) 100 ml of 2% acetone in hexane.

(3) 100 ml of 6% acetone in hexane.

(4) 500 ml of 10% acetone in hexane.

Fractions were collected (100 ml each) and all were revealed by TLC (10% acetone in hexanes). Fractions containing different products were separately combined and evaporated to dryness under reduced pressure.

$^1$H-NMR (CDCl$_3$, #16-#25): 5.56 (1H, m), 5.39 (1H, m), 3.62 (s, 3H), 3.599 (1H, m), 2.322 (2H, t), 2.227 (2H, m), 2.053 (2H, m), 1.609 (2H, m), 1.478 (2H, m), 1.296 (16H, m) and 0.854 (3H, t) ppm.

c. Hydrolysis of ricinoleic acid methyl ester: 55 grams of ricinoleic acid methyl ester (0.176 mole) was dissolved in 200 ml of methanol. To the solution it was added NaOH (35.2, 0.88 mole) dissolved in 200 ml of DDW. The mixture was stirred for 5 h at 40° C. (water bath). After, the mixture was diluted with DDW (600 ml) and acidified with concentrated HCl solution to a final pH of 2. the mixture was extracted with ethyl acetate (200 ml), treated with anhydrous MgSO$_4$, filtered and evaporated to dryness.

Yield=47.5 grams (~90%), TLC (10% acetone/hexanes)=0.08.

$^1$H-NMR (CDCl$_3$) showed the disappearance of the peak at 3.62 which confirmed the complete removal of the methyl ester protecting group.

Method II: Purification of Ricinoleic Acid by Precipitation of the Sodium Salt of Ricinoleic Acid by an Anti-solvent.

To 10.36 g of the crude ricinoleic acid (Fluka, <85% of ricinoleic acid) was added 20 ml of ethanol containing 3.76 g KOH (molar ratio RA:KOH 1:2). This mixture was allowed to stir for a few hours at room temperature to form a precipitate of the Potassium salt of Ricinoleic acid. The ethanol was evaporated until dry solid was obtained. The weight of the obtained solid was 13.9 g. To this solid was added 44 ml of di-isopropyl ether containing 10% of Ethanol (in the ratio 1:4.4 between weight of RA and washing solution). This mixture was shaken vigorously in order to obtain a homogeneous dispersion. The dispersion was centrifuged at 2000 rpm (aprox.) for 20 min. As a result of centrifugation, clear separation of the two phases (solid and liquid) occurred. The supernatant that had brown color was decanted and the obtained precipitate (mainly white) was washed again by the same amount of the washing liquid and separation by centrifugation was performed. The total loss after the two washing procedures was in the range of 15%. Alternatively, the ethanol solvent was not evaporated, instead isopropyl ether was added to obtain a 85:15 v/v ratio with the ethanol. The solids were separated by centrifugation, as above. The solid was dissolved in 70 ml of the DDW and acidified by concentrated HCl to pH=1. As a result of acidification a layer of liquid oil was separated on the top of the water phase. The oil phase was separated from the water phase without extraction and dissolved in 20 ml of the ethyl acetate or acetone. This solution was washed by 50 cc of DDW, separated and treated by anhydrous magnesium sulfate (drying agent) and activated carbon (discoloring agent) by mixing for 10 min at room temperature, which was followed by mixing at 60° C. for additional 15 min. The treated solution was filtrated through two paper filters with cotton between them in order to trap particles of magnesium sulfate and activated carbon.

Ethyl acetated was evaporated to yield a clear very slightly yellowish oil (about 60% overall yield) which contain >95% ricinoleic acid as determined by HPLC analysis.

Other methods for purification such as conjugation to a solid support or a hydrophilic component or esterification with a bulky molecule at the hydroxyl side group of ricinoleic acid as described above were used but were found less efficient than the above methods.

Example 2

Synthesis and Characterization of -alkyl Ricinoleic Acid Terminated Polyanhydrides Materials:

Ricinoleic acid, (85% content, technical, Fluka, Buch, Switzerland), acetic anhydride (Merck, Darmstadt, Germany), Meth-Prep II, methanol esterification reagent (Altech, Deerfield, Ill.), were used in this study. All solvents were analytical grade from Aldrich (Milwaukee, Wis.) or Frutarom (Haifa, Israel).

Infrared (IR) spectroscopy (Perkin Elmer System 2000 FT-IR) was performed on monomer, prepolymer, and polymer samples cast onto NaCl plates from dichloromethane solution. Thermal analysis was determined on a Metler TA 4000-DSC Differential Scanning Calorimeter (DSC), calibrated with Zinc and Indium standards, at a heating rate of 10° C./min. Molecular weights of the polymers were estimated on a Size Exclusion Chromatography (SEC) system consisting of a Spectra Physics (Darmstadt, Germany) P1000 pump with UV detection (Applied Bioscience 759A Absorbance UV detector) at 254 nm, a Rheodyne (Coatati, Calif.) injection valve with a 20 μl loop, and a Spectra Physics Data Jet integrator connected to a computer. Samples were eluted with CHCl$_3$ through a linear Styrogel column (Waters, 10 Å pore size) at a flow rate of 1 ml/min. The molecular weights were determined relative to polystyrene standards (Polyscience, Warrington, Pa.) with a molecular weight range of 400 to 1,500,000 using a WINner/286 computer program. $^1$H NMR spectra (CDCl$_3$) were obtained on a Varian 300 MHz spectrometer using CDCl$_3$ as solvent and tetramethylsilan (TMS) as reference. Catalytic hydrogenation was carried out with 3% palladium on carbon powder using a Parr 3911EK hydrogenation apparatus (Parr Inst. Moline Ill., USA). Fatty acid degradation products were esterified using an esterification reagent Meth-Prep II, and determined by gas chromatography (GC) using a Perkin Elmer 1020 plus GC, with a Silar 10C chromatographic column (Alltech) and FID detector using a temperature gradient of 5° C./min from 140° C. to 240° C.

Non-Linear Fatty Acid Synthesis:

5 g of ricinoleic acid (17 mmole) were dissolved in 75 ml of anhydrous CH$_2$Cl$_2$ and placed in a 250 ml round bottomed flask. After addition of 3 ml pyridine (34 mmole) the solution was cooled to about 0° C. by immersing in an ice-water bath, and 34 mmole of the fatty acid chloride in CH$_2$Cl$_2$ (40 ml) were added dropwise. The mixture was warmed to room temperature and stirred for two days. The solvent was evaporated and 500 ml of anhydrous ether were added to the residue. A white precipitate was formed, which was removed by filtration. Ether was removed by rotevaporation and 100 ml of anhydrous CH$_2$Cl$_2$ were added. The CH$_2$Cl$_2$ layer was washed three times with 200 ml of aqueous NaHCO$_3$ and two times with double distilled water (DDW). The CH$_2$Cl$_2$ layer was dried over MgSO$_4$, and the solvent was removed by roto-evaporation. Chromatography of 3 g of this product was performed on a silica gel column (60 g silica mesh 70-230) using petroleum ether/ethyl acetate (80/20 v/v) mixture as eluent to yield 1.2 g of the clean product as determined by TLC. The following esters were synthesized by this procedure:

Ricinoleic Acid Stearyl Ester (RASTE)

IR (cm$^{-1}$) 2900 and 2850 (C—H stretching bands), 1710 (carbonyl); $^1$H NMR 5.50 (m, 1H, CH$_2$—CH=CH—CH$_2$), 5.30 (m, 1H, CH$_2$—CH=CH—CH$_2$), 4.90 (quintet, 1H, OCO—CH), 2.50 (m, 2H, (CH$_2$)$_{15}$—CH$_2$—COO—CH), 2.40 (m, 2H, CH$_2$—COOH), 2.30 (m, 2H, OCO—CH—CH$_2$—CH=CH), 2.00 (m, 2H, HC=CH—CH$_2$—CH$_2$), 1.60 (m, 2H, CH$_2$—CH$_2$—COOH), 1.50 (m, 2H, OCO—CH—CH$_2$—CH$_2$), 1.35 (m, 46H, 23 CH$_2$'s), 0.90 (t, 3H, Me).

Ricinoleic Acid Myristoyl Ester (RAMYRE)

IR (cm$^{-1}$) 2900 and 2850 (C—H stretching bands), 1710 (carbonyl); $^1$H NMR 5.50 (m, 1H, CH$_2$—CH=CH—CH$_2$), 5.30 (m, 1H, CH$_2$—CH=CH—CH$_2$), 4.90 (quintet, 1H, OCO—CH), 2.50 (m, 2H, (CH$_2$)$_{15}$—CH$_2$—COO—CH), 2.40 (m, 2H, CH$_2$—COOH), 2.30 (m, 2H, OCO—CH—CH$_2$—CH=CH), 2.00 (m, 2H, HC=CH—CH$_2$—CH$_2$), 1.60 (m, 2H, CH$_2$—CH$_2$—COOH), 1.50 (m, 2H, OCO—CH—CH$_2$—CH$_2$), 1.35 (m, 38H, 19 CH$_2$'s), 0.90 (t, 3H, Me).

Ricinoleic Acid Lauryl Ester (RALAUE)

IR (cm$^{-1}$) 2900 and 2850 (C—H stretching bands), 1710 (carbonyl); $^1$H NMR 5.50 (m, 1H, CH$_2$—CH=CH—CH$_2$), 5.30 (m, 1H, CH$_2$—CH=CH—CH$_2$), 4.90 (quintet, 1H, OCO—CH), 2.50 (m, 2H, (CH$_2$)$_{15}$—CH$_2$—COO—CH), 2.40 (m, 2H, CH$_2$—COOH), 2.30 (m, 2H, OCO—CH—CH$_2$—CH=CH), 2.00 (m, 2H, HC=CH—CH$_2$—CH$_2$), 1.60 (m, 2H, CH$_2$—CH$_2$—COOH), 1.50 (m, 2H, OCO—CH—CH$_2$—CH$_2$), 1.35 (m, 34H, 17 CH$_2$'s), 0.90 (t, 3H, Me).

Ricinoleic Acid Octanoyl Ester (RAOCTE)

IR (cm$^{-1}$) 2900 and 2850 (C—H stretching bands), 1710 (carbonyl); $^1$H NMR 5.50 (m, 1H, CH$_2$—CH=CH—CH$_2$), 5.30 (m, 1H, CH$_2$—CH=CH—CH$_2$), 4.90 (quintet, 1H, OCO—CH), 2.50 (m, 2H, (CH$_2$)$_{15}$—CH$_2$—COO—CH), 2.40 (m, 2H, CH$_2$—COOH), 2.30 (m, 2H, OCO—CH—CH$_2$—CH=CH), 2.00 (m, 2H, HC=CH—CH$_2$—CH$_2$), 1.60 (m, 2H, CH$_2$—CH$_2$—COOH), 1.50 (m, 2H, OCO—CH—CH$_2$—CH$_2$), 1.35 (m, 26H, 13 CH$_2$'s), 0.90 (t, 3H, Me).

Prepolymer Synthesis

The prepolymer of sebacic acid (SA) was prepared from the purified diacid monomer by refluxing in excess acetic anhydride for 30 minutes and evaporating the solvent to dryness. The hot clear viscous residue was dissolved in an equal volume of dichloromethane and precipitated in a mixture of ether/petroleum ether (1:1 v/v). The white precipitate was collected by filtration and dried by vacuum at room temperature. Acetyl terminated fatty acid anhydrides were prepared by dissolving the acids in acetic anhydride (120° C., 1:5 w/v) and refluxing for 20 min. Acetate anhydrides of oleic acid, linoleic acid and other cis-double bond containing fatty acid were prepared by refluxing the fatty acid in acetic anhydride for 20 min. and evaporating the solvent to dryness to obtain a liquid. Mixed prepolymers of diacids with the monoacid terminals were prepared similarly.

Preparation of Ricinoleic Acid-oligo Lactide Ester

Ricinoleic acid or Na or Ca salt was dissolved in toluene containing lactide at a 1:1 to 1:10 molar ratio. To the solution, a catalytic amount of Sn-octoate was added and the solution was left to polymerize over night at reflux. The solvent was evaporated and the residue oligomers were purified by dissolving the residue in a minimal amount of dichloromethane and precipitated in ethanol or propanol. The precipitate was isolated by filtration. Ricinoleic acid esters with lactic acid chains attached by an hydroxyl of the ricinoleic acid by an ester bond were obtained. Products with oligomeric lactic acid chains of 2-5 lactic acid are liquids of pastes. Similarly, other cyclic lactones including glycolide, caprolactone, and trimethylene carbonates, were reacted with ricinoleic acid by ring opening to form oligo hydroxy acids on the side chain. These products can be used as monomers to be inserted in a polyanhydride or polyesters.

Polymer Synthesis:

Polymers were prepared by melt condensation of the prepolymers at 150° C. Typically, fatty acid acetate anhydride (70 g) and SA prepolymer (30 g) were placed in a 50 ml round bottom flask equipped with a magnetic stirrer and a vacuum line port. The prepolymers were melted in an 150° C. oil bath before connecting the system to a vacuum line. The polymerization was continued for 2 hour under a vacuum of 0.5 mm Hg with constant stirring. The polymerization was followed by GPC analysis of samples withdrawn from the polymerization flask during polymerization. The polymers have typical IR absorption at 1740 and 1810 cm$^{-1}$ (symmetrical and asymmetrical anhydride C=O stretching bands). Terminated polymers with oleic acid, linoleic acid or linolenic acid terminals with dodecandioic acid, sebacic acid, isophthalic acid, and other diacid and triacid monomers were prepared under similar conditions to form pleable and reproducible polymers.

In Vitro Hydrolytic Degradation of Polymers:

The in vitro hydrolysis was evaluated by injecting 0.1 g samples of polymers in 10 ml of 0.1M phosphate buffer pH 7.4 at 37° C. with constant shaking (100 REV). The polymer became semisolid in the buffer. At each time point, the solution was replaced with fresh buffer. The hydrolysis of the polymer was monitored by (a) weight loss of the sample, (b) disappearance of the anhydride bonds by IR spectroscopy, and (c) changes in molecular weight of the polymer by SEC. The degradation products (fatty acids) were extracted from the aqueous phase by adding 1 ml of chloroform and vortexing for 1 min. The organic phase was collected and dried by a stream of nitrogen, followed by 2 h of lyophilization to remove all traces of water. The dry residue was dissolved in a solution mixture composed of 50 μl toluene, 10 μl methanol and 20 μl Meth-Prep II, methanol esterification reagent. The solution containing the derivatized acids was analyzed by gas chromatography using a Silar 10C chromatographic column using a temperature gradient of 5° C./min from 140 to 240° C. [12].

In Vitro Drug Release:

Drugs such as paclitaxel, methotrexate (MTX), 5-FU, aminocycline, gentamicin, amphotericin B, (5, to 30 weight %) were incorporated in the polymer by mixing the drug powder in the liquid polymer and loaded in a syringe. Drug release studies were conducted by injecting each polymer sample in 20 ml phosphate buffer 0.1M pH 7.2 at 37° C. with continuous shaking (100 REV). The drug concentration in the solution was determined by UV detection at the relevant wave length or by HPLC.

Polymer Stability:

Stability was conducted by placing samples of polymers at −10° C., 4° C. and 25° C. under argon atmosphere, and monitoring the changes in molecular weight for a period of three months. The effect of the storage conditions on the drug release was determined.

Polymer Synthesis:

Purified ricinoleic acid (>95%) was transformed into a non-linear fatty acid by esterification with oleyl chloride in the presence of pyridine. $^1$H-NMR spectrum of ricinoleic acid oleate show peak at 4.9-5 ppm attributed to the methine μ to the ester, indicating successful esterification. No impurities of the ricinoleic starting material which, usually appear at 4.7 ppm (μ11 dehydration impurity), 3.6 ppm (unreacted ricinoleic acid) and 2.78 ppm (linoleic acid) are seen in the spectrum. Non-linear fatty acid terminated poly(sebacic anhydride) were synthesized by melt condensation to yield waxy off-white materials. All polymers have typical IR absorption at 1740 and 1810 cm$^{-1}$ (symmetrical and asymmetrical anhydride C=O stretching bands). The physical properties of poly(sebacic acid) terminated with 70 and 80% by weight of ricinoleic acid oleate were pasty at room temperature with a molecular weight in the range of 1,000 to 3,000.

In Vitro Hydrolysis of Polymers

The weight average molecular weight of the degraded samples were monitored by GPC, a sharp decrease in molecular weight was observed during the first 48 h, followed by a slow degradation phase which kept the Mw at 1000 for another 7 days. The polymer lost about 50% of its initial weight after 6 days, During this period which last for about one week, the relatively water soluble component, sebacic acid, is released from the solidified paste leaving the hydrophobic component, ricinoleic acid based non-linear fatty acid, which is slow to solubilize.

Liquid polymers were obtained when linolenyl-ricinoleic acid was reacted with sebacic acid is a 70:30 w/w ratio or higher content of ricinoleic acid terminals. Saturated fatty acid esters of ricinoleic acid with chain length of 10 methylenes or shorter were liquids at room temperature when polymerized with sebacic acid at a 70:30 w/w ratio.

Example 3

Synthesis of Oleic Acid Terminated Polyanhydrides

Oleic acid was mixed with the following diacids: sebacic acid, ricinoleic acid maleate, polyethylene glycol dicarboxylic acid (Mw=1000), isophthalic acid, terephthalic acid, fumaric acid, poly(lactic acid) dicarboxylic acid (Mw=1700), poly(lactic-glycolic acid) (Mw=1500), and polycaprolactone dicarboxylic acid (Mw=2000). The amount of oleic acid increased from 50% by weight to 80% and the mixtures were dissolved in acetic anhydride (1:10 w/w) and refluxed for 30 min. The solvent was evaporated to dryness and the residue was vacuum polymerized at 150° C. for 2 hours (0.1 mm Hg) to form a viscous melt which solidified at room temperature. The melting points of the various polymers ranged from 30 to 65° C.

Polymers with mixed terminals were prepared by mixing the oleic acid with non-linear or linear mono carboxylic acids to obtain polymers with different properties.

Example 4

Poly(ester-anhydrides) with Ricinoleic Acid in the Polymer Backbone

Materials

Ricinoleic acid, technically 85% pure (Fluca, Buch, Switzerland); sebacic acid 99% pure (Aldrich Milwaukee, Wis.); acetic anhydride (Merck, Darmstadt, Germany) were used in this study. All solvents were analytical grade from Aldrich (Milwaukee, Wis.) or Frutarom (Haifa, Israel).

Methods

The prepolymer of sebacic (SA) acid was prepared from purified diacid monomer by refluxing in excess (1:5 w/v) acetic anhydride for 30 min with constant stirring and evaporating the solvent to dryness. The hot clear viscous residue was dissolved in an equal volume of dichloromethane and precipitated in a mixture of ether/petroleum ether (1:1 v/v). The white precipitate was collected by filtration and dried by vacuum at room temperature. The polymer of SA (PSA) was prepared by melt condensation of the prepolymer at 160° C. The polymerization was continued for 3 hours under a vacuum of 0.1 mmHg with constant stirring. The polymerization was followed by GPC analysis of samples withdrawn from the polymerization flask during polymerization every 30 min. The final molecular weight was 36000. The polymer has typical IR absorption at 1740 and 1810 cm$^{-1}$ (symmetrical and asymmetrical anhydride C=O stretching bands.

The poly(ester-anhydrides) were prepared in a one-pot reaction in two steps: (a) transesterification: typically, PSA and ricinoleic acid of different purities were dissolved in excess toluene in dry 100 ml round-bottomed flask equipped with a mechanical stirrer and Dean-Stark glassware. The reaction took place at 120° C. followed by GPC analysis of withdrawn from the reaction flask during the reaction. The reaction was stopped as soon as the product achieved minimal stable molecular weight (according to the theory). The duration of the transesterification reaction was 1.5-3 hours depending on the kind and percentage of hydroxy acid. (b) polymerization: the off-white paste product (prepolymer) was dissolved in acetic anhydride (1:1 w/v) and refluxed for 30 min. The solvent was evaporated to dryness. The poly(ester-anhydrides) were prepared by melt condensation of the prepolymer at 160° C. The polymerization was continued for 1.5-4 hours under a vacuum of 0.1 mmHg with constant stirring. Duration of the polymerization depended on theoretical molecular weight of the final product. The polymerization was followed by GPC analysis of samples withdrawn from the polymerization flask during polymerization every 30 min. Ricinoleic acid based poly(ester-anhydrides) are yellow liquids at PSA-RA 3:7 and 2:8 polymers polymer unit ratio.

Spectroscopy Analysis:

All the polymers of that kind have typical IR absorption at 1740 and 1810 cm$^{-1}$ (symmetrical and asymmetrical anhydride C=O stretching bands and at 1050-1300 cm$^{-1}$ (ester C—O stretching bands). All the ricinoleic acid based poly(ester-anhydrides) have typical NMR peaks at 4.95 ppm (quintet, 1H OCO—CH) and at 2.43 ppm (triplet, 6H (2H of ricinoleic acid and 4H of sebacic acid) $CH_2$—$CH_2$—COOCO). Those peaks indicate presence of ester and anhydride bonds in the product. All the spectrum lacks a peak at 3.64 ppm (m, 1H $CH_2$—CHOH—$CH_2$). According to NMR spectrum there is no free ricinoleic acid in the final product.

The molecular weights and melting points of the poly(anhydride-ester) of ricinoleic acid-sebacic acid are listed in Table 1.

TABLE 1

| Monomer ratio | index | Mn | Mw | m.p. |
| --- | --- | --- | --- | --- |
| p(PSA-RA)3:7 | PA-MK-137i | 8,400 | 9,000 | liquid |
| p(PSA-RA)2.5:7.5 | PA-MK-137ii | 6,200 | 7,100 | liquid |
| p(PSA-RA)2:8 | PA-MK-137iii | 4,300 | 5,100 | liquid |

The ricinolecic acid-sebacic acid anhydride-ester copolymers are liquids at room temperature depending on the ricinoleic acid content.

Polymer Stability:

Anhydride bonds are moisture sensitive and therefore anhydride-containing polymers are usually stored at freezing temperatures under argon or nitrogen atmosphere. In addition, these polymers may undergo inter and intra anhydride interchange, which result in a decrease in Mw upon storage. The stability of pasty poly(PSA-RA) was studied by placing samples of the pasty polymers (70 mg) in glass bottles under nitrogen atmosphere and stored at −17° C., 4° C. and 25° C. Changes in molecular weight of these poly(ester-anhydrides) were determined for a period of 6 months. After 6 month the polymers, stored at −17° C., 4° C. and 25° C. still retained their initial molecular weight.

Stability to γ-Irradiation:

The expected application of these poly(ester-anhydrides) is as implantable or injectable drug carriers. It is therefore essential to properly sterilize the device prior the administration. The most effective method for the terminal sterilization of moisture and heat sensitive polymers is exposure to ionization radiation. The irradiation resistance of various microorganisms varies with the type of organism; it is currently thought that a radiation dose of 2.5 Mrad is sufficient for the sterilization of medical implants. Previous publications indicated that polyanhydrides are stable to γ-irradiation for an extended time period. Pasty/liquid poly(PSA-RA) were exposed to γ-irradiation at a dose of 2.5 Mrad at room temperature.

Samples of pasty polymers of the same weight were irradiated at room temperature with an absorbed dose of 2.5 Mrad by means of a $^{60}$Co source (450000 Ci; 16 hours). The irradiation was conducted at Sor-Van Radiation Ltd. (Nachal Sorek, Yavne, Israel). All pasty polymers are freely injectable at 37° C. (melt at 24-33.6° C.) and have a molecular weight of 2,000 to about 6,000. No change in the molecular weight was observed. To eliminate the possibility for irradiation crosslinking, the solubility of the polymers in dichloromethane before and after irradiation was determined (120 mg of polymer in 1 ml of solvent). All samples dissolved immediately at room temperature to form a clear solution. No difference was observed in thermal behavior (Tm, ΔH), color and shape of the irradiated and non-irradiated polymer samples.

Incorporation of Paclitaxel in the Liquid Polymer, in vitro and Toxicity Studies In vitro Drug Release Paclitaxel was incorporated in the polymer without affecting the polymer molecular weight or chemically interacting with the polymer, as confirmed by GPC and $^1$H-NMR. The in vitro release of paclitaxel is affected by the drug content. Increasing the loading decreases the release rate, which is expected when incorporating the highly hydrophobic paclitaxel. The rate of paclitaxel release from the pasty polymer differs as the function of the drug loaded in the polymer. As the percentage of paclitaxel is higher in the polymer the rate of the release is slower. Formulation containing 5% of paclitaxel released 33% of the incorporated drug in 3 months, formulation containing 10% released 20% of its content, and formulation containing 20% of paclitaxel released only 9% in 3 months. As the content of paclitaxel in the polymer increases, the formulation becomes more hydrophobic and does not allow water to penetrate and dissolve the drug and degrade the polymer. On the other hand, what matters is the amount of paclitaxel that is released and available to kill the malignant cells. Thus, in this manner, high content of paclitaxel delays the degradation of polymer and it may release the drug over longer period of time.

Toxicity of Polymer-Paclitaxel Implant

Three groups of mice were injected with increasing amounts of 10% paclitaxel loaded formulation. In the groups where mice received 250-mg/kg and 500 mg/kg paclitaxel all mice survived the entire period of the experiment and gained weight similar to the controls. In the 1000 mg/kg group 2 mice died after 1 week and 2 mice died after 2 weeks. Mortality, probably, is related to the extremely high dose of the paclitaxel, being at least an order of magnitude higher than the maximum tolerated dose (MTD) for paclitaxel in mice[15] (the MTD of paclitaxel in female SPF C3H/HeNcrj mice (8 weeks, 20±3 g) was determined to be 26 mg/kg after intravenous injection. Death due to toxicity was observed at a dose of 30-mg/kg of paclitaxel (Kim S C, Kim D W, Shim Y H, Bang J S, Oh H S, Kim S W. In vivo evaluation of polymeric micellar paclitaxel formulation: toxicity and efficacy. Journal of Controlled release 2001, 72(1-3): 191-202)).

Based on these results, the estimated tolerated dose for mice is at least 100 mg of formulation containing 10% of paclitaxel or 500 mg/kg.

Histopathological evaluation indicated that in the 3 groups in which paclitaxel loaded formulation was added to the polymer, the degree of inflammation was generally not higher than the control group, suggesting no adverse reaction upon application of the combined therapeutic modality. No evidence of any active inflammatory reaction or tissue irritation extending beyond the local capsule was noted. The local tissue reaction typically consisted of thin enveloping capsule, interpreted as scarring reaction, occasionally associated with minimal to mild presence of inner amorphous, perhaps necrotic material. No evidence of granulomatous foreign-body, or lymphoid cell aggregation was noted, indicating well tolerability, including lack of immunological stimulation.

Example 5

Preparation of Poly(ester-anhydride) Based on Ricinoleic Acid Oligoesters

Ricinoleic acid oligomers of 2 to 10 monomer units were prepared by melt condensation of purified ricinoleic acid as follows: chromatography purified ricinoleic acid (98% pure, 10 g) was dissolved in 50 ml toluene and refluxed for 2 hours. Toluene was evaporated to dryness and the residue was melt polymerized under vacuum for 4 hours to form a viscous oil having a molecular weight of 1,800. This oligomer was incorporated into poly(sebacic acid), Mw=45,000 by a transesterification reaction and repolymerization with acetic anhydride. The polymers composed of 70% w/w ricinoleic acid oligomers were liquid at room temperature. Alternatively, ricinoleic acid oligomers were prepared from the melt condensation of the cyclic lactone of ricinoleic acid.

Anticancer drugs, paclitaxel, 5-FU, MTX, cisplatin and carboplatin, were incorporated into the polymer to form pasty injectable formulations. The release of drugs from these polymers was in general slower than the release obtained from the ricinoleic acid based poly(ester-anhydride) under similar conditions. Other therapeutic agents active in treating solid tumors, including peptides, proteins, oligonucleotides, polynucleotides and plasmids, have also been released from the polymer formulations. These macromolecular agents are incorporated in the polymer by direct mixing or first interact these active agents with polycations and stabilizing agents prior to incorporation in the polymer.

Another related liquid polymer is prepared from the ring opening polymerization of lactide and other lactones initiated by the hydroxy group of ricinoleic acid. Short oligomers were attached to ricinoleic acid hydroxy group. The product was allowed to polymerize to a polyester-anhydride by melt condensation using acetic anhydride. Other cyclic esters have been applied to form ricinoleic acid with oligomeric side groups.

Example 7

Release of Paclitaxel from Poly(ester-anhydrides)

The in vitro release of paclitaxel from various compositions of poly(ester-anhydrides) based on ricinoleic acid was determined. The effects of the following factors were investigated: (1) purity of the ricinoleic acid used for making the polymer carrier; (2) paclitaxel particle size and dispersing agents added to the formulation; (3) additives to the paclitaxel-polymer formulation; and (4) preencapsulation of paclitaxel into nanoparticles and microparticles.

Effect of Ricinoleic Acid Purity

The effect of the purity of ricinoleic acid on the consistency and the release of paclitaxel was studied. Pasty poly(sebacic acid-ricinoleic acid) 30:70 were prepared by the one-pot method from the reaction between poly(sebacic acid), Mw=40,000 and ricinoleic acid of different purities at a 30:70 w/w ratio. Ricinoleic acid purified by the chromatography method or the by the extraction method (described above), purified ricinoleic acid by chromatograph containing 5% w/w of stearic acid or a mixture of 5% w/w stearic acid and 10% oleic acid, crude ricinoleic acid obtained from Fluka were used. The polymer prepared from the purified ricinoleic acid was clear slightly yellowish liquids at room temperature with a molecular weight in the range of 6,000. Increasing the molecular weight increases the viscosity of the polymer. The polymers prepared from crude ricinoleic acid were yellowish viscous liquids, more viscous than that the polymers prepared from purified RA but still injectable. Paclitaxel at a 5%, 10% and 15% w/w was incorporated into these polymers by well mixing the drug powder until a uniform thin formulation is obtained. The formulations are pasty with increasing viscosity as the amount of paclitaxel is increased. The polymers prepared from the purified ricinoleic acid were less viscous and easily injectable even at 15% drug loading, the formulations prepared from the polymers prepared from technical RA were more viscous but still injectable if warmed at 35° C.

The pasty formulations at 5% w/w drug loading were injected into a large volume of 0.1M phosphate buffer pH7.4 at 37° C. and the paclitaxel release to the solution was determined as a function of time. Paclitaxel was released at a constant rate of about 0.75% per day of the loaded drug from the polymers prepared from the crude ricinoleic acid, while the release from the polymers prepared from purified ricinoleic acid was a little faster, 0.90% per day.

Effect of Surfactants and Mixing Procedures

In order to obtain a uniform and reproducible dispersion of the drug in the polymer, paclitaxel was mixed with the following surfactants at a 1:1 and 1:3 weight ratio: Tween 80, Span 20, phosphatidylcholine, poloxamer, cremophor, and polyethylene glycol 400. The drug mixtures were then mixed in the polymer at a 5% w/w drug to polymer ratio. Except for phosphatidylcholine, uniform dispersions were obtained. The surfactant slightly improved the uniformity of the formulation. In a second experiment, paclitaxel was dissolved in minimal amount of ethanol and mixed in the polymer to yield a very uniform milky formulation. The release of drug from these formulations was a little slower than that obtained for the untreated paclitaxel with the most effect obtained with the formulation prepared using ethanol solution which showed about 30% decrease in the release rate in vitro.

Effect of Additives

Hydrophilic additives including: short chain polyethylene glycol, poloxamer, and thin powder of sugars or salts, were added to the formulation at the amount of 5-30% of the formulation compositions. Paclitaxel was released faster from these formulations for the first few days but the release become to almost the same as without the additives.

Effect of Pre-encapsulation

Paclitaxel was encapsulated into lipid nanoparticles at a 30% drug loading by melt mixing of solid triglycerides, paclitaxel and phospholipids in warm 5% dextrose water solution. The uniform nanodispersion was freeze dried to a powder. The powder was mixed in the liquid polymer to form the formulation. Paclitaxel was release at a slower rate compared to the paclitaxel powder.

This study was repeated for methotrexate, cisplatin and 5-FU with improvement in the dispersity and uniformity.

Example 8

Combination with Other Drugs

The combination of two or more anticancer agents in the polymer implant was investigated. The release of a combination of drugs from liquid formulations of poly(sebacic-ricinoleic ester anhydride) was studied using a 1:1 w/w mixture of cisplatin or carboplatin with paclitaxel. The release of paclitaxel was slightly enhanced as compared to the paclitaxel alone and the release of platin drugs was slower that platin alone. This is explained by the increased hydrophobicity of the device by the highly hydrophobic paclitaxel molecules. The increase of the paclitaxel content increases the hydrophobicity. Other drugs such as cyclosporin, verapamil, rapamycine and other drugs that may help overcome the MDR effect if occurred was incorporated along with paclitaxel or other anticancer agents. These drugs were released constantly from the device parallel to the release of paclitaxel with the release time depending on the water solubility of the incorporated drugs. Peptidic and protein drugs as well as DNA molecules active in treating solid tumors were also incorporated in the liquid polymers and were released for weeks under in vitro conditions.

Example 9

Treatment of Cancer

Human prostate cancer cell lines (LuCAP-35, WISH-2, $1 \times 10^6$ cells in 100µ) were injected subdermally into the back of the mice. Follow-up included palpation and measurement of the tumor every two days. When the tumor reached a size of about 5×5 mm, a dose of polymer was injected under the tumor and the size of the tumor was monitored. Four substances: carboplatin, paclitaxel, combination of the two drugs, and the combination with the MDR inhibitor cyclosporine were used. Three doses of the polymer-drug compositions were tested.

In all cases, the tumor size decreased dramatically within one week with no death of mice. To the contrary, the animals treated with placebo polymer or systemic drug administration did not affect the growing rate of the tumor. The animals of the control group died during the first 20 days after inoculation.

In a second experiment, Copenhagen rats were used with the MatLyLu cell line. The lower abdomen was shaved, and a transverse incision made above the pubic bones. The abdominal muscles were divided, the intestine lifted up and the ventral lobe of the prostate exposed inferior to the bladder. A MatLyLu cell suspension in 100μ was injected into the ventral lobe using an insulin syringe and a 26G needle. The abdominal muscles were closed with 3/0 vicryl suture, and the skin with 3/0 silk. Several days later (as obtained from the kinetic studies) the rats were anesthetized and operated on the same way. The pasty polymer loaded with the drug was injected into the growing tumor in the ventral lobe of the prostate. The rat was sacrificed 5-20 days later. The prostate and lymph nodes were fixed in 10% formalin.

This study showed a significant reduction in tumor size over time.

In a third experiment, C3H nude mice were injected with about one million human bladder cancer cells to induce a tumor. Within five days a detectable solid tumor was recognized. A liquid polymer composed of poly(sebacic acid-ricinoleic acid ester-anhydride) 30:70 w/w ratio loaded with 5% paclitaxel, a 5 mg dose of paclitaxel, was injected under the tumor and the tumor size was monitored for the next 6 weeks. As control, polymer injection without drug was used.

The mice treated with the drug loaded polymer showed a decrease in tumor size with time while the animals treated with the drug free polymer showed a rapid increase in tumor size to about 30,000 mm$^3$ at day 25 from less than 100 mm$^3$ at day 5.

Example 10

Preparation Of Polyester Pastes

Purified ricinoleic acid (97% pure, prepared as described above, 10 g) was mixed with dry lactic acid (15 g) in toluene (50 ml). The mixture was heated to reflux with stirring for one hour and the solvent was evaporated. The clear oily residue was left in a 130° C. oil bath with stirring for 8 hours under a vacuum of 0.5 mmhg. The viscosity was increased with time. The formed polymer was a paste at room temperature having a molecular weight of Mw=6,500. In a similar way, ricinoleic acid was reacted with different ratios of lactic acid, glycolic acid, hydroxy butyric acid, and their mixtures.

Alternatively, poly(lactic acid), PLA, containing ricinoleic acid in the polymer backbone was prepared by transesterification of ricinoleic acid and PLA (Mw=24,000) at a 10:90 ratio to 50:50 w/w ratio. The reaction was in a glass flask at 130° C. for 5 hours under dry nitrogen environment. The polymers obtained were pasty to allow injection from a syringe.

Example 11

Release of Drugs From Poly(RA-SA) Liquid Polymer

Drugs fine powders including: risporidol, tetracycline, chlorhexidin, and aminocycline were mixed at room temperature at a 20% w/w loading. The drugs were release in 0.1M phosphate buffer pH7.4 by adding 100 microlitter of the polymer-drug mixture in a vial having 3 ml of buffer at 37° C. The medium was replaced with fresh buffer every 1-3 days and drug released to the releasing medium was determined by UV detection or HPLC. The drugs were releases in a constant manner for at least 10 days.

Example 12

Release of Peptides

Insulin powder (200 mg) was mixed in liquid poly(SA-RA) 30:70 (800 mg) at room temperature. The uniform formulation was added in buffer solution (100 mg in 50 ml phosphate buffer pH7.4 at 37° C.) and the release of insulin to the solution was determined by HPLC. A constant release of insulin for more than 30 days was obtained. Similar results were obtained for the peptides, LHRH, somatostatin, TRH, and growth hormone.

Example 13

Incorporation of Nanoparticles and Microparticles in Poly(SA-RA) 20:80

Complexes of GFP plasmid DNA with polyethyleneimine of a 200 nanometer particle size were mixed in liquid poly (SA-RA) 20:80. The mixture is used for the controlled delivery of DNA over time.

Nanospheres of PLA-GA loaded with small and large drug molecules such as paclitaxel, bupivacaine, or gentamicin prepared by common methods are mixed in the liquid polymer. The release of drug from the liquid formulation occurs in two steps, release from the particles and then diffusion through the viscous polymer.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

I claim:

1. A drug delivery composition comprising a biodegradable, aliphatic poly(ester-anhydride) copolymer comprising random ester bonds along the polyanhydride backbone and a biologically active agent, wherein the copolymer is prepared by transesterification of a poly(anhydride).

2. The composition of claim 1, wherein the biologically active agent is selected from the group consisting of small drug molecules, peptides and proteins, DNA and DNA complexes with cationic molecules.

3. The composition of claim 2, wherein the biologically active agent is selected from the group consisting of the group consisting of antibacterial, anti-inflammatory and anticancer agents, antidepressants, analgesics and local anesthetics.

4. The composition of claim 1, wherein the composition is in a form suitable for administration by injection.

5. The composition of claim 1, wherein the poly(ester-anhydride) comprises one or more monomers derived from a hydroxy acid or dicarboxylic acid selected from the group consisting of C4 to C22 linear alkane dicarboxylic acids, dimer erucic acid, dimer oleic acid, ricinoleic acid, non-linear fatty acid-esters of ricinoleic acid, oligomers or polymers of hydroxyl acids, O-esters and carbonates of ricinoleic acid, oligo(hydroalkanoic acid)-O-esters and carbonates of ricinoleic acid, hydroxyl-acid terminated oligomers containing a ricinoleic acid terminal, and mixtures thereof.

6. The composition of claim 5, wherein the poly(ester anhydride) copolymer comprises monomers derived from a dicarboxylic acid selected from the group consisting of dodecanedioic acid and sebacic acid and comonomers derived from ricinoleic acid, non-linear fatty acid-esters of ricinoleic acid, oligomers or polymers of hydroxyl acids, O-esters and carbonates of ricinoleic acid, oligo(hydroalkanoic acid)-O-esters and carbonates of ricinoleic acid, hydroxyl-acid terminated oligomers containing a ricinoleic acid terminal, and mixtures thereof.

7. The composition of claim 6, wherein the polymer is terminated with a fatty acid selected from the group consisting of ricinoleic acid, oleic acid, linoleic acid, and linolenic acid.

8. The composition of claim 5, wherein the poly(ester anhydride) comprises monomers, oligomers, polymers, or combinations thereof derived from sebacic acid and monomers derived from ricinoleic acid.

9. The composition of claim 8, wherein the polymer is prepared from purified ricinoleic acid, wherein ricinoleic acid comprises at least 90% by weight of the polymer.

10. The composition of claim 8, wherein the poly(ester anhydride) is formed from monomers, oligomers, polymers, or combinations thereof derived from sebacic acid and monomers derived from ricinoleic acid.

11. The composition of claim 5, wherein the hydroxy acid is an oligomer or polymer of hydroxy acids.

12. The composition of claim 11, wherein the hydroxy acid is selected from the group consisting of lactic acid, glycolic acid, hydroxybutyric acid, hydroxycaproic acid, hydroxybenzoic acid, mucic acid, tartaric acid, pentahydroxycyclohexane carboxylic acid and combinations thereof.

13. The composition of claim 1, wherein the biologically active agent is encapsulated in microparticles or nanoparticles.

14. A drug delivery composition comprising a biodegradable poly(ester-anhydride) copolymer comprising random ester bonds along the polyanhydride backbone and a biologically active agent, wherein the poly(ester anhydride) comprises monomers derived from ricinoleic acid and sebacic acid, and wherein the copolymer is prepared by transesterification of a poly(anhydride).

15. The composition of claim 14, the polymer is a copolymer of sebacic acid and ricinoleic acid.

16. The drug delivery composition of claim 15, wherein the ratio of monomers derived from ricinoleic acid to monomers derived from sebacic acid is 8:2 or 7:3.

17. The composition of claim 14, wherein the biologically active agent is selected from the group consisting of small drug molecules, peptides and proteins, DNA and DNA complexes with cationic molecules.

18. The composition of claim 17, wherein the biologically active agent is selected from the group consisting of the group consisting of antibacterial, anti-inflammatory and anticancer agents, antidepressants, analgesics and local anesthetics.

19. The composition of claim 14, wherein the composition is in a form suitable for administration by injection.

20. The composition of claim 14, wherein the polymer is prepared from purified ricinoleic acid, wherein ricinoleic acid comprises at least 90% by weight of the polymer.

21. The composition of claim 14, wherein the biologically active agent is encapsulated in microparticles or nanoparticles.

* * * * *